United States Patent [19]

Bredeweg et al.

[11] 4,117,007
[45] Sep. 26, 1978

[54] ERADICATION OF BIS-CHLOROMETHYL ETHER AND 1,1,1,2-TETRACHLOROETHANE FROM CHLOROACETYL CHLORIDE

[75] Inventors: Robert A. Bredeweg; Yog R. Dhingra, both of Midland, Mich.

[73] Assignee: The Dow Chemical Company, Midland, Mich.

[21] Appl. No.: 842,831

[22] Filed: Oct. 17, 1977

[51] Int. Cl.$^2$ .............................................. C07C 51/42
[52] U.S. Cl. ............................................... 260/544 Y
[58] Field of Search ................................... 260/544 Y

[56] References Cited

U.S. PATENT DOCUMENTS 4,054,602  10/1977  Dhingra .......................... 260/544 Y Primary Examiner—Gerald A. Schwartz
Attorney, Agent, or Firm—G. R. Plotecher

[57] ABSTRACT

Bis-chloromethyl ether (CME) and 1,1,1,2-tetrachloroethane (TCE) impurities are efficiently eradicated from chloroacetyl chloride (CAC) by a process comprising contacting the CAC, containing about 100 to about 250 ppm CME and about 1 weight percent, based on the weight of the CAC, of TCE, with a catalytic amount of ferric and/or aluminum cations at a temperature at least about 50° C. This process does not require hydrochloric acid and yields CAC containing less than detectable (<0.5 ppm CME, <0.05 wt. % TCE) amounts of the impurities.

8 Claims, No Drawings

ERADICATION OF BIS-CHLOROMETHYL ETHER AND 1,1,1,2-TETRACHLOROETHANE FROM CHLOROACETYL CHLORIDE

BACKGROUND OF THE INVENTION

1. Field of the Invention:

This invention relates to chloroacetyl chloride, chloroacetyl chloride in combination with various impurities, and a process for eradicating the impurities from chloroacetyl chloride.

2. Description of the Prior Art:

Larsen et al., U.S. Pat. No. 3,674,664, teach a method of preparing chloroacetyl chloride (CAC) by photochemically oxidizing vinylidene chloride. While this process is industrially attractive, it does produce small (100–250 ppm) amounts of bis-chloromethyl ether (CME), an impurity and a known carcinogen, and 1,1,1,2-tetrachloroethane (TCE), also an impurity but of considerably less toxicity. Since CAC is used as an intermediate in the manufacture of various pesticides and pharmaceuticals, it is desirable to eradicate as much of the CME and TCE from the CAC as possible. Moreover, higher production costs are experienced because CME- and TCE-contaminated CAC prohibits CAC recycle because of CME and TCE accumulation. Consequently, more waste is experienced.

The preferential eradication of CME and TCE from CAC is not amenable to most chemical and physical separation methods. CAC and CME are sufficiently similar in their chemical reactivities and CAC, TCE and CME are sufficiently similar in their physical properties to render conventional separation methods, such as selective absorption, azeotropic or fractional distillation, or complexing, generally ineffective.

Dhingra, "Removal of Bis-Chloromethyl Ether from Chloroacetyl Chloride", Ser. No. 728,103 and filed Sept. 30, 1976 teaches removal of CME from CAC by a process comprising contacting a mixture comprising CAC and CME with hydrochloric acid at a temperature between about 30° C and about 160° C in the presence of a catalytic amount of a Lewis or strong protic acid, such as aluminum chloride or oleum. The Dhingra teaching differs from the present invention in that the presence of hydrochloric acid is critical to the Dhingra process whereas it is noncritical to the present invention.

SUMMARY OF THE INVENTION

According to this invention, both CME and TCE are effectively eradicated from CAC by a process comprising contacting a mixture comprising CAC, CME and TCE with a catalytic amount of ferric and/or aluminum cations at a temperature of at least about 50° C. The CME and TCE are eradicated to less than detectable levels with little or no adverse effect to the CAC. "Less than detectable levels" here means that the CME is eradicated to less than 0.5 ppm and the TCE is eradicated to less than 0.05 weight percent (based upon the weight of CAC). "Eradicated" and like terms here mean that the CME and TCE are converted to other compounds (presumably chloromethylchloroacetate and trichloroethylene, respectively) which are readily removed from the CAC by conventional methods, such as distillation. The resulting, substantially CME- and TCE-free CAC can either be used as such or flash distilled or otherwise treated to remove the residual catalyst and converted impurities. If flash distilled, the CAC can be recovered in excess of 98.5 percent purity and the catalytic residue recycled.

DETAILED DESCRIPTION OF THE INVENTION

The ferric and aluminum cations here used can be generated from any suitable source. Typically, these cations are generated from their chloride salts, such as $FeCl_3$, $Fe_2Cl_6$, $AlCl_3$, $Al_2Cl_6$, hydrated or anhydrous, but other suitable sources include ferric and aluminum fluorides, bromides, iodides, sulfates, acetates, tosylates, oxalates, nitrates, benzoates, phosphates, etc.; ferric and aluminum oxides; iron and aluminum filings; and the like. Ferric cations are preferred to aluminum cations and iron filings, ferric oxide and ferric chloride are the preferred sources of ferric cations. The latter are preferred because the anion of the other sources (bromides, acetates, etc.) may exchange with the chloride of the CAC and thus result in new impurities and loss of CAC. Ferric chloride is an especially preferred source. The ferric and aluminum cations can be used either singly (which is preferred) or in combination with one another.

Catalytic amounts of these cations are used. For example, if ferric chloride ($FeCl_3$) is the catalyst, then at least about 0.05, and preferably about 0.25, weight percent (based upon the CAC) is the typical minimum amount of catalyst employed. Practical considerations, such as catalyst recovery, economics and general convenience, are the only limitations on the maximum amount of catalyst that can be used. For $FeCl_3$, about 2, and preferably about 0.75, weight percent is typically the maximum amount of catalyst employed. Typical equivalent amounts for aluminum or other ferric materials can be calculated.

Use of various surface-area catalysts such as retrol clay, zeolites, silica gels, carbon and the like, can optionally be combined with the cations to enhance the rate of reaction (eradication). However, use of a surface-area catalyst alone will not substantially reduce the levels of either CME or TCE.

The typical minimum temperature which the CME- and TCE-contaminated CAC is contacted with the cations is at least about 50° C and preferably at least about 70° C. A typical maximum temperature is about 140° C and preferably about 115° C. Temperatures in excess of 140° C can be used to accelerate the CME and TCE decomposition, but such temperatures generally result in CAC degradation. Of course, temperatures in excess of about 105° C (reflux temperature) require ampule conditions.

A typical minimum residence time is about 15 minutes and preferably about 30 minutes with a maximum residence time determined by practical considerations but generally of about 120 minutes and preferably about 60 minutes duration. Of course, residence time can vary according to initial CME and TCE levels, temperature and catalyst. Reduction of CME and TCE levels generally begins within minutes after reaching the typical minimum temperature, and this is especially true if a surface-area catalyst is present.

Pressure is not critical to this invention except for its relationship to temperature. Autogenous pressures are generally sufficient. Preferably, the process is conducted at reflux conditions (105° C, atmospheric pressure) because under pressure, the reaction rate decreases.

Although this invention is generally concerned with eradicating CME and TCE from a mixture of CAC, CME and TCE wherein the initial levels of CME are approximately 100-250 ppm and TCE approximately 1 weight percent (based upon the weight of the CAC), this invention is adaptable to situations where the initial levels exceed (e.g. 1000 ppm CME and 5 wt. percent TCE) these amounts by adjusting the catalyst concentration. Generally, the more impurity present, the more catalyst employed.

The following examples are illustrative of certain specific embodiments of this invention. Unless otherwise indicated, all parts and percentages are by weight.

Specific Embodiments

EXAMPLE 1

CAC (100 g) containing 100 ppm of CME and 0.81 percent TCE was mixed with anhydrous ferric chloride (0.4 g). The mixture was refluxed at approximately 105° C and continuously stirred. Samples were taken at 30-minute intervals for gas chromatographic (GC) analysis. The results are reported in Table I.

TABLE I

CME AND TCE ERADICATION FROM CAC BY CONTACTING WITH FeCl$_3$

| Time Interval[1] (Min.) | CME (ppm)[2] | TCE (wt. %)[3] |
|---|---|---|
| 30 | 31 | 0.57 |
| 60 | <0.5 | <0.05 |
| 90 | <0.5 | <0.05 |

[1]Time zero = commencement of heating.
[2]Detection threshold = 0.5 ppm.
[3]Detection threshold = 0.05 wt. %.

EXAMPLES 2-5

Example 1 was quadruplicated except that both the concentration of ferric chloride and the reaction temperature were allowed to vary. The results are reported at Table II.

TABLE II

CME AND TCE ERADICATION FROM CAC BY CONTACTING WITH FeCl$_3$ AT VARIOUS FeCl$_3$ CONCENTRATIONS AND REACTION TEMPERATURES

| FeCl$_3$ concentration (wt. %)[1]: | 0.065 | | 0.215 | | | 0.37 | | 0.49 |
|---|---|---|---|---|---|---|---|---|
| Impur.[2] | Time Interval[3] Min. | Temperature (° C) | | | | | | |
| | | 105 | 90 | 105 | 120 | 90 | 105 | 120 | 90 |
| CME (ppm)[4] | 0 | 91.0 | 91 | 91.0 | 91.0 | 91.0 | 91.0 | 91.0 | 99.0 |
| | 30 | — | 56 | 21.0 | 1.3 | 37.0 | 8.4 | 0.6 | <0.5 |
| | 60 | 37.0 | 38 | 7.0 | <0.5 | 21.0 | 0.7 | — | — |
| | 90 | 19.0 | 27 | 2.6 | <0.5 | 9.0 | <0.5 | — | — |
| | 150 | 9.0 | — | — | — | — | — | — | — |
| TCE (wt. %)[5] | 0 | 0.71 | — | 0.81 | 0.81 | 0.81 | — | — | — |
| | 30 | — | — | 0.54 | <0.05 | 0.7 | — | — | — |
| | 60 | 0.64 | — | 0.37 | 0.05 | 0.62 | — | — | — |
| | 90 | 0.55 | — | 0.26 | 0.05 | 0.56 | — | — | — |
| | 150 | 0.47 | — | — | — | — | — | — | — |

[1]Based on the weight of CAC
[2]Impurity
[3]Time zero = commencement of heating.
[4]Detection threshold = 0.5 ppm.
[5]Detection threshold = 0.05 weight %.

EXAMPLE 6

Effect of Hydrochloric Acid on Catalyst Residue Recycle

CAC (300 g) containing 100 ppm of CME and 0.81 percent TCE was mixed with anhydrous ferric chloride (1.1 g) and refluxed at approximately 105° C for about 60 minutes while continuously stirred. A crude product (297.4 g) was transferred to a flash still where approximately 285 g of essentially (>99 percent pure) CME- and TCE-free CAC was recovered.

A catalytic residue (8.97 g) was recovered from the bottom of the still and mixed with fresh CAC (288 g). The fresh CAC contained 100 ppm CME and 0.81 percent TCE. The mixture was then divided into two equal portions. The first portion was refluxed at about 105° C while continuously stirred for about 60 minutes in the presence of HCl (continuously sparged through the first portion at sufficient rate to saturate CAC). GC analysis of the crude product reported the presence of 65 ppm CME and 0.6 percent TCE.

The second portion was similarly refluxed and stirred but in the absence of HCl. GC analysis of this crude product reported 38 ppm CME and 0.68 percent TCE.

These results demonstrate that the catalytic residue contains only a partial activity as compared to a fresh catalyst. The results also demonstrate that hydrochloric acid is not necessary to the practice of this invention, and if anything, is somewhat deleterious as regards CME eradication at reflux conditions.

EXAMPLE 7 AND CONTROLS A-C

Samples of CAC (100 g) containing CME (100 ppm) and TCE (0.81 percent) were individually mixed with various Lewis acids. The resulting mixtures were refluxed and continuously stirred for about 2 hours and then analyzed by GC. The results are reported in Table III.

TABLE III

EFFECT OF VARIOUS LEWIS ACIDS ON CME AND TCE ERADICATION FROM CAC

| Example | Lewis Acid | Conc. (%) | CME (ppm) | TCE (%) |
|---|---|---|---|---|
| 7 | AlCl$_3$ | 1.1 | 17 | <0.05 |
| Control | | | | |
| A | SnCl$_4$ | 1.2 | 98 | 0.80 |
| B* | ZnCl$_2$ | 1.0** | 102 | 0.81 |
| C* | CuCl$_2$ | 1.1** | 91 | 0.81 |

*Reflux at about 105° C for 90 minutes and at about 85° C for 120 minutes.
**Slurry. Lewis Acid did not dissolve completely.

EXAMPLE 8

CAC (100 g) containing CME (100 ppm) and TCE (0.81 percent) was mixed with Fe$_2$O$_3$ (1.1 percent). The resulting slurry (not all the Fe$_2$O$_3$ dissolved) was then refluxed for 2 hours while continuously stirred. GC analysis detected about 0.1 ppm CME and did not detect TCE.

EXAMPLE 9

Example 8 was repeated except iron filings were substituted for $Fe_2O_3$ and the resulting slurry was refluxed for 90 minutes and then 85° C for 120 minutes instead of at 105° C for 2 hours. GC analysis detected 8 ppm CME and 0.45 percent TCE.

EXAMPLES 10-13

Example 1 was again quadruplicated except that in Examples 11-13 the mixture was continuously sparged with various gases. Example 10 was not sparged, i.e., it is a duplicate of Example 1. The results are reported at Table IV.

TABLE IV
SPARGE EFFECTS ON CME
AND TCE ERADICATION FROM CAC

| Ex. | Sparge Gas | Imp.[1] | Time (min) | | | |
|---|---|---|---|---|---|---|
| | | | 0 | 60 | 90 | 150 |
| 10 | None | CME (ppm): | 100 | 13.0 | 3.4 | 0.7 |
| | | TCE (wt. %): | 0.81 | 0.46 | 0.31 | 0.20 |
| 11 | $N_2$ | CME (ppm): | 100 | 37.0 | 19.0 | 9.0 |
| | | TCE (wt. %): | 0.81 | 0.64 | 0.55 | 0.47 |
| 12 | Air | CME (ppm): | 100 | 7.3 | 1.8 | <0.5 |
| | | TCE (wt. %): | 0.81 | 0.42 | 0.30 | 0.19 |
| 13 | HCl | CME (ppm): | 140 | 10.8 | 3.8 | — |
| | | TCE (wt. %): | 0.70 | 0.52 | 0.43 | — |

[1]impurity

EXAMPLE 14

Example 6 was repeated except that the mixtures of fresh CAC and catalytic residue contained about 3.3 percent residue and both mixtures were heated under ampule conditions (temperature in excess of 105° C, autogenous pressure). Subsequent GC analysis showed that the mixture containing added HCl had 84 ppm CME and 0.54 percent TCE while the mixture without added HCl had 55 ppm CME and 0.71 percent TCE. These results are consistent with the results of Example 6 and also indicate that the presence of HCl on CME eradication is more detrimental under ampule conditions than reflux conditions. The latter is probably due to the fact that under reflux conditions, HCl is continually escaping and thus not as much is present as under ampule conditions.

EXAMPLES 15-18

CAC (100 g) containing 100 ppm of CME was mixed with various amounts of $FeCl_3$. The resulting mixtures were heated for various times under ampule conditions at various temperatures and subsequently analyzed by GC. The results are reported at Table V.

TABLE V
CME ERADICATION FROM CAC
UNDER AMPULE CONDITIONS

| Ex. | $FeCl_3$ (wt. %) | Time (hr) | Temp. (°C) | HCl | CME (ppm) |
|---|---|---|---|---|---|
| 15 | 0.24 | 1 | 125 | yes | 2.1 |
| 16 | 0.04 | 1 | 125 | yes | 39.0 |
| 17 | 0.21 | 1 | 120 | no | <0.5 |
| 18 | 0.21 | 0.5 | 120 | no | 1.3 |

EXAMPLE 19

Example 1 was repeated except that $Fe_2(SO_4)_3$ (0.5%) was substituted for $FeCl_3$. After two hours, GC analysis did not detect either CME or TCE.

Although this invention has been described in considerable detail through the preceding Examples, these examples are for purposes of illustration only, and variations can be made without departing from the spirit of the invention or the scope of the adjoining claims.

what is claimed is:

1. A process of eradicating bis-chloromethyl ether and 1,1,2-tetrachloroethane from a mixture comprising chloroacetyl chloride, bis-chloromethyl ether and 1,1,2-tetrachloroethane, the process consisting essentially of contacting, in the absence of hydrochloric acid, the mixture with a catalytic amount of ferric and/or aluminum cations at a temperature of at least about 50° C.

2. The process of claim 1 wherein the mixture is contacted with ferric cations.

3. The process of claim 2 wherein the ferric cations are generated from ferric chloride, ferric oxide or iron filings.

4. The process of claim 2 wherein the ferric cations are generated from ferric chloride.

5. The process of claim 3 wherein ferric chloride is present in an amount of at least about 0.05 weight percent based upon the weight of chloroacetyl chloride.

6. The process of claim 3 wherein ferric chloride is present in an amount of at least about 0.25 weight percent based upon the weight of chloroacetyl chloride.

7. The process of claim 6 wherein the contacting is conducted at a temperature of at least about 70° C.

8. The process of claim 6 wherein the contacting is conducted at reflux conditions.

* * * * *